United States Patent
Yang

(10) Patent No.: US 6,479,513 B2
(45) Date of Patent: *Nov. 12, 2002

(54) ANTICANCER COMPOUND AND ENANTIOMER SEPARATION METHOD USEFUL FOR SYNTHESIZING SAID COMPOUND

(75) Inventor: Bingwei V. Yang, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/761,994

(22) Filed: Jan. 17, 2001

(65) Prior Publication Data

US 2002/0004514 A1 Jan. 10, 2002

Related U.S. Application Data

(60) Provisional application No. 60/177,718, filed on Jan. 21, 2000.

(51) Int. Cl.⁷ ............... A61K 31/47; C07D 215/16; C07D 215/20
(52) U.S. Cl. .................... 514/312; 546/158
(58) Field of Search .................. 514/312; 546/158

(56) References Cited

U.S. PATENT DOCUMENTS 6,150,377 A    11/2000   Lyssikatos et al.
6,258,824 B1 *  7/2001   Yang

FOREIGN PATENT DOCUMENTS

WO      9716443     5/1997
WO      9721701     6/1997

* cited by examiner

*Primary Examiner*—D. Margaret Seaman
(74) *Attorney, Agent, or Firm*—Peter C. Richardson; Paul H. Ginsburg; Jeffrey N. Myers

(57) ABSTRACT

The present invention relates to the compound (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, pharmaceutically acceptable salts and solvates thereof, prodrugs thereof, and to the use of said compound for inhibiting abnormal cell growth, including cancer, in mammals. The invention also relates to methods useful in synthesizing the aforementioned compound.

8 Claims, No Drawings

US 6,479,513 B2

ANTICANCER COMPOUND AND ENANTIOMER SEPARATION METHOD USEFUL FOR SYNTHESIZING SAID COMPOUND

This invention claims the benefit priority of U.S. Provisional Application No. 60/177,718, filed Jan. 21, 2000.

BACKGROUND OF THE INVENTION

This invention relates to a compound that can be used in the treatment of hyperproliferative disease, such as cancer, in mammals. This invention also relates to a method of using this compound, namely (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, in the treatment of hyperproliferative disease in mammals, especially humans, and to pharmaceutical compositions containing these enantiomers. This invention further relates to a method of separating enantiomers in a racemic mixture from one another, which method can be utilized to obtain the aforementioned compound of the invention.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo famesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., *Science*, Vol. 260, 1834 to 1837, 1993, incorporated herein in its entirety by reference). The compound of the present invention exhibits activity as an inhibitor of the enzyme farnesyl protein transferase and therefore is believed to be useful as an anti-cancer and anti-tumor agent. Further, the compound of the present invention may be active against any tumors that proliferate by virtue of farnesyl protein transferase.

The racemate 6-[amino-(6-chloro-pyridin-3-yl)-(3-methyl-3H-imidazol-4-yl )-methyl]-4-(3-chloro-phenyl)-1-cyclopropylmethyl-1H-quinolin-2-one and other compounds that can inhibit farnesyl protein transferase are disclosed in U.S. patent application Ser. No. 09/501,163, filed Feb. 9, 2000, and in International Publication No. WO 00/47574, both of which are hereby incorporated by reference in their entireties.

Other compounds that are indicated as having activity inhibiting farnesyl protein transferase are referred to in International Publication Number WO 97/21701, entitled "Farnesyl Protein Transferase Inhibiting (Imidazol-5-yl) methyl-2-quinolinone Derivatives", which has an International Publication Date of Jun. 19, 1997; in International Publication Number WO 971/6443, entitled "Farnesyl Transferase Inhibiting 2-Quinolone Derivatives", which has an International Publication Date of May 9, 1997; PCT/IB99/01393, filed Aug. 5, 1999, entitled "2-Quinolone derivatives Useful as Anticancer Agents"; and PCT/IB99/01398, filed Aug. 6, 1999, entitled "Alkynyl-Substituted Quinolin-2-one Derivatives Useful as Anticancer Agents"; all of which are incorporated herein by reference in their entireties.

SUMMARY OF THE INVENTION

The present invention relates to the compound (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one and to pharmaceutically acceptable salts and solvates thereof, and to prodrugs thereof.

"(+)-6-[Amino-(6-chloro-pyridin-3-yl)-(3-methyl-3H-imidazol-4-yl)-methyl]-4-(3-chlorophenyl)-1-cyclopropylmethyl-1H-quinolin-2-one" refers to the dextrorotatory isomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one. The dextrorotatory isomer of 6-[amino-(6-chloropyridin-3-yl)-(3-methyl-3H-imidazol-4-yl)-methyl]-4-(3-chloro-phenyl)-1-cyclopropylmethyl-1H-quinolin-2-one has been found to have greater activity in inhibiting the enzyme farnesyl protein transferase than the levorotatory isomer. The term "(+)-6-[amino-(6-chloro-pyridin-3-yl)(3-methyl-3H-imidazol-4-yl)-methyl]-4-(3-chloro-phenyl)-1-cyclopropylmethyl-1H-quinolin-2-one" for purposes of the present invention and unless otherwise indicated herein, however, also refers to compositions consisting essentially of (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one substantially free of (−)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, the levorotatory isomer of 6-[amino -(6-chloro-pyridin-3-yl)-(3-methyl-3H-imidazol-4-yl)-methyl]-4-(3-chloro-phenyl)-1-cyclopropylmethyl-1H-quinolin-2-one. The term "substantially free" means that the amount of the dextrorotatory isomer predominates the composition relative to the levorotatory isomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one. More specifically, this means that the amount of the dextrorotatory isomer relative to the levorotatory isomer by weight is at least about 90%, preferably greater than about 95%, more preferably greater than about 99%.

The phrases "racemate", "racemic mixture", and other like phrases refer to generally equimolar proportions of a levorotatory isomer and a dextrorotatory isomer of a compound in a composition.

This invention also relates to a method of inhibiting abnormal cell growth in a mammal comprising administering to said mammal an amount of the aforementioned compound of the invention, or a pharmaceutically acceptable salt or solvate or prodrug thereof, that is effective in inhibiting farnesyl protein transferase.

This invention also relates to a method of inhibiting abnormal cell growth in a mammal comprising administering to said mammal an amount of the aforementioned compound of the invention, or a pharmaceutically acceptable salt or solvate or prodrug thereof, that is effective in inhibiting abnormal cell growth.

This invention further relates to a method of inhibiting abnormal cell growth in a mammal which comprises administering to said mammal an amount of the aforementioned compound of the invention, or a pharmaceutically acceptable salt or solvate or prodrug thereof, in combination with an amount of a chemotherapeutic, wherein the amounts of the compound, salt, solvate, or prodrug, and the chemotherapeutic are together effective in inhibiting abnormal cell growth. Several chemotherapeutics are known in the art, and these can be used in the present invention. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of the aformentioned compound of the invention, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compound of the invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of the compound of the invention, pharmaceutically acceptable salt or solvate thereof, or prodrug thereof, which amount is effective in sensitizing abnormal cells to treatment with radiation. The amount of the compound, salt, solvate, or prodrug in this method can be determined according to the means for ascertaining effective amounts of the compound of the invention described herein.

This invention further relates to a pharmaceutical composition for inhibiting abnormal cell growth in a mammal comprising an amount of the aforementioned compound of the invention, or a pharmaceutically acceptable salt or solvate or prodrug thereof, that is effective in inhibiting farnesyl protein transferase, and a pharmaceutically acceptable carrier.

This invention further relates to a pharmaceutical composition for inhibiting abnormal cell growth in a mammal comprising an amount of the aforementioned compound of the invention, or a pharmaceutically acceptable salt or solvate or prodrug thereof, that is effective in inhibiting abnormal cell growth, and a pharmaceutically acceptable carrier.

This invention also relates to a pharmaceutical composition for inhibiting abnormal cell growth in a mammal which comprises an amount of the aforementioned compound of the invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens, and a pharmaceutically acceptable carrier.

This invention also relates to a method of and to a pharmaceutical composition for inhibiting abnormal cell growth in a mammal which comprises an amount of the compound of the invention, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the compound of the invention in the methods and pharmaceutical compositions described herein. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl) -amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl) -amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl) -amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa -bicyclo[3.2.1]octane-3-carboxylic acid hydroxyamide;

3-endo-3-[4-(4-fluoro-phenoxy)-benzenesulfonylamino]-8-oxa -bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

The compound of the present invention can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restenosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "pharmaceutically acceptable salt(s)", as used herein, unless otherwise indicated, includes salts of groups of the compound of the invention, which groups are capable of forming salts. For example, pharmaceutically acceptable salts include hydrochloride salts of the amino group and/or the imidazolyl group of the compound. Other pharmaceutically acceptable salts of the amino group and/or imidazolyl group are hydrobromide, sulfate, hydrogen sulfate, phosphate, hydrogen phosphate, dihydrogen-phosphate, acetate, succinate, citrate, tartrate, lactate, mandelate, methanesulfonate (mesylate) and p-toluenesulfonate (tosylate) salts. The preparation of such salts is described below.

The subject invention also includes isotopically-labelled compounds, which compounds are identical to the above recited compound of the invention, but for the fact that one or more atoms thereof are replaced by an atom having an atomic mass or mass number different from the atomic mass or mass number usually found in nature. Examples of isotopes that can be incorporated into the compound of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the invention, and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in- some circumstances. Isotopically labelled compounds of this invention can generally be prepared by carrying out the procedures disclosed in the Schemes and/or in the Examples below, by substituting a readily available isotopically labelled reagent for a non-isotopically labelled reagent. Accordingly, reference to the compound of the invention for use in the therapeutic methods and pharmaceutical compositions described herein also encompasses isotopically-labelled forms of the compound.

This invention also encompasses prodrugs of the compound (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, and pharmaceutical compositions containing and methods of treatment through administering such prodrugs. For example, the free amino group of the compound can be converted into a prodrug. Such prodrugs include compounds wherein an amino acid residue, or a polypeptide chain of two or more (e.g., two, three or four) amino acid residues is covalently joined through an amide or ester bond to the free amino group. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, omithine and methionine sulfone. A prodrug comprising a carbamate of the amino group is also included as part of the invention. The free amine can also be derivatized as an amide, sulfonamide or phosphonamide to form a prodrug. All of these prodrug moieties may incorporate groups including but not limited to ether, amine and carboxylic acid functionalities.

Patients that can be treated with the compound of the invention, or pharmaceutically acceptable salts or solvates thereof, or a prodrug thereof, or isotopically labelled compounds of the invention, according to the methods of this invention include, for example, patients that have been diagnosed as having lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), neoplastic cutaneous diseases (e.g. psoriasis, mycoses fungoides), or Barrett's esophagus (pre-malignant syndrome).

The compound of the invention, its pharmaceutically acceptable salts and solvates, its prodrugs, and its radioactively-labelled derivatives can all independently also furthermore be used in a palliative neo-adjuvant/adjuvant therapy in alleviating the symptoms associated with the diseases recited in the preceding paragraph as well as the symptoms associated with abnormal cell growth. Such therapy can be a monotherapy or can be in a combination with chemotherapy and/or immunotherapy.

Patients that can be treated according to the methods of this invention also include patients suffering from abnormal cell growth, as defined above.

This invention also relates a method of separating (+) and (−) enantiomers of a compound of formula 1 in a racemic mixture,

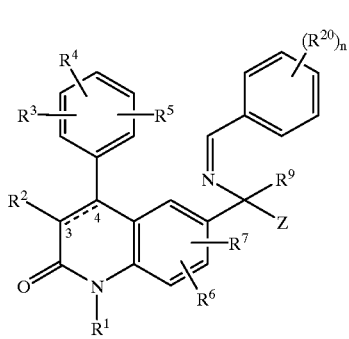

1 wherein:
the dashed line indicates an optional second bond connecting C-3 and C-4 of the quinolin-2-one ring;
$R^1$ is selected from H, $C_1$–$C_{10}$ alkyl, —$(CR^{13}R^{14})_qC(O)R^{12}$, —$(CR^{13}R^{14})_qC(O)OR^{15}$, —$(CR^{13}R^{14})_qOR^{12}$, —$(CR^{13}R^{14})_qCSO_2R^{15}$, —$(CR^{13}R^{14})_t(C_3$–$C_{10}$ cycloalkyl), —$(CR^{13}R^{14})_t(C_6$—$C_{10}$ aryl), and —$(CR^{13}R^{14})_t$(4—10 membered heterocyclic), wherein said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;

$R^{12}$ is halo, cyano, —C(O)OR$^{15}$, or a group selected from the substituents provided in the definition of $R^{12}$;

each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2,— (CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, $C_1$–$C_{10}$ alkyl, $C_2$–$C_{10}$ alkenyl, $C_2$–$C_{10}$ alkynyl, —(CR$^{13}$R$^{14}$)$_t$(C$_6$–C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 $R^6$ substituents;

$R^9$ is —(CR$^{13}$R$^{14}$)$_t$(imidazolyl) or —(CR$^{13}$R$^{14}$)$_t$(pyridinyl) wherein said imidazolyl or pyridinyl moiety is substituted by 1 or 2 $R^6$ substituents each $R^{12}$ is independently selected from H, $C_1$–$C_{10}$ alkyl, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —C(O)R$^3$, —C(O)OR$^{13}$, OC(O)R$^3$, —NR$^{13}$C(O)R$^{14}$, —C(O)NR$^{13}$R$^{14}$, —NR$^{13}$R$^{14}$, hydroxy, $C_1$–$C_6$ alkyl, and $C_1$–$C_6$ alkoxy;

each t is independently an integer from 0 to 5 and each q is independently an integer from 1 to 5;

each $R^{13}$ and $R^{14}$ is independently H or $C_1$–$C_6$ alkyl, and where $R^{13}$ and $R^{14}$ are as —(CR$^{13}$ $^{R14}$)$_q$ or —(CR$^{13}$R$^{14}$)$_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and -SiR$^{17}$R$^{18}$R$^{19}$;

$R^{17}$, $R^{18}$ and $R^{19}$ are each independently selected from the substituents provided in the definition of $R^{12}$ except at least one of $R^{17}$, $R^{18}$ and $R^{19}$ is not H;

$R^{20}$ is H, $C_1$–$C_{10}$ alkyl, $C_2$$C_{10}$ alkenyl, $C_2$–$C_{10}$ alkynyl, halo, nitro, trifluoromethyl, trifluoromethoxy, —OR$^{12}$, —OC(O)R$^{12}$, —C(O)R$^{12}$, —NR$^{12}$, R$^{13}$, —NR$^{13}$C(O)R$^{12}$, —C(O)NR$^{12}$R$^{13}$ cyano, —C(O)OR$^{13}$, —SR$^{12}$, or —(CR$^{13}$R$^{14}$)$_t$(C$_6$—C$_{10}$ aryl), wherein said aryl $R^{20}$ group is substitute by 1 to 4 $R^6$ groups; and n is an integer selected from 1 to 3;

which method comprises applying a portion or all of said racemic mixture to a chiral separation apparatus, under conditions suitable for separation of chiral molecules, and obtaining the separated (+) and (−) enantiomers of formula 1 from said apparatus, subsequent to said conditions.

The compounds of formula 1 have utility in that they are believed to inhibit the enzyme farnesyl protein transferase. Also, the compounds of formula 1 encompass intermediate compounds useful for synthesizing (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, the compound of the invention.

The phrase "chiral separation apparatus" includes apparatuses capable of separating chiral molecules. Apparatuses capable of separating chiral molecules are known in the art, including columns containing material capable of binding (+) and (−) enantiomers of a given chiral compound differentially such that the (+) and (−) enantiomers elute from the column at different rates. Several columns useful for separation of (+) and (−) enantiomers of chiral molecules are commercially available, and any of these could be used in the present invention. Examples of such columns include, but are not limited to, CHIRALCEL™ OD and CHIRAL-PAK™ AD (both from Daicel Chemical Industries, LTD (Osaka, Japan)).

Conditions suitable for separation of chiral molecules are conditions such as temperature and eluent, and such conditions are related to the particular apparatus selected for separating the enantiomers. Such conditions can be determined by a person of ordinary skill in the art.

The subject invention also relates to a method of synthesizing a (+) or (−) enantiomer of formula 2

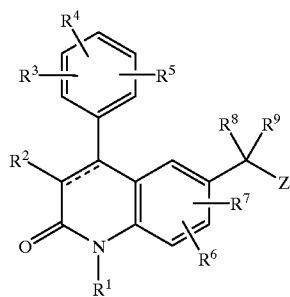

2 wherein:

the dashed line indicates an optional second bond connecting C-3 and C-4 of the quinolin-2-one ring;

$R^1$ is selected from H, $C_1$–$C_{10}$ alkyl, —(CR$^{13}$R$^{14}$)$_q$C(O)R$^{12}$, —(CR$^{13}$R$^{14}$)$_q$C(O)OR$^{15}$, —(CR$^{13}$R$^{14}$)$_q$OR$^{12}$, —(CR$^{13}$R$^{14}$)$_q$(CSO$_2$R$^{15}$, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic), wherein said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;

$R^2$ is halo, cyano, —C(O)OR $^{15}$, or a group selected from the substituents provided in the definition of $R^{12}$;

each $R^3$, $R^4$, $R^5$, $R^6$, and $R^7$ is independently selected from H, $C_1$–$_{C10}$alkyl, $C_2$–$C_{10}$ alkenyl, $C_2$–$C_{10}$alkynyl, halo, cyano, nitro, trifluoromethyl, trifluoromethoxy, azido, —OR$^{12}$—C(O)R$^{12}$, —C(O)OR$^{12}$,—NR$^{13}$C(O) OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$,—CH=NOR$^{12}$, —S(O)$_j$R$^{12}$ wherein j is an integer from 0 to 2,—(CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$; and wherein the cycloalkyl, aryl and heterocyclic moieties of the foregoing groups are optionally fused to a C$_6$–C$_{10}$ aryl group, a C$_5$–C$_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, C$_1$–C$_{10}$ alkyl, C$_2$C$_{10}$ alkenyl, C$_2$–C$_{10}$ alkynyl, —(CR$^{13}$R$^{14}$)$_t$(C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 R$^6$ substituents;

R$^8$ is —NH$_2$, —NH(C$_1$–C$_{10}$ alkyl), or —N(C$_1$–C$_{10}$ alkyl)(C$_1$–C$_{10}$ alkyl);

R$^9$ is —(CR$^{13}$R$^{14}$)$_t$(imidazolyl) or —(CR$^{13}$R$^{14}$)$_t$(pyridinyl) wherein said imidazolyl or pyridinyl moiety is substituted by 1 or 2 R$^6$ substituents;

each R$^{12}$ is independently selected from H, C$_1$–C$_{10}$ alkyl, —(CR$^{13}$R$^{14}$)$_t$(C$_3$–C$_{10}$cycloalkyl), —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic R$^{12}$ groups are optionally fused to a C$_6$–C$_{10}$ aryl group, a C$_5$–C$_8$ saturated cyclic group, or a 4–10 membered heterocyclic group; and the foregoing R$^{12}$ substituents, except H but including any optional fused rings, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$—NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy;

each t is independently an integer from 0 to 5 and each q is independently an integer from 1 to 5;

each R$^{13}$ and R$^{14}$ is independently H or C$_1$–C$_6$ alkyl, and where R$^{13}$ and R$^{14}$ are as —(CR$^{13}$R$^{14}$)$_q$or —(CR$^{13}$R$^{14}$), each is independently defined for each iteration of q or t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^9$; and, R$^{17}$, R$^{18}$ and R$^{19}$ are each independently selected from the substituents provided in the definition of R$^{12}$ except at least one of R$^{17}$, R$^{18}$ and R$^{19}$ is not H;

which method comprises a) obtaining a racemic mixture comprising (+) and (–) enantiomers of a compound of formula 1

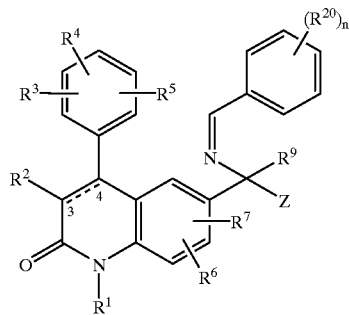

wherein R$^{20}$ is H, C$_1$–C$_{10}$ alkyl, C$_2$–C$_{10}$ alkenyl, C$_2$–C$_{10}$ alkynyl, halo, nitro, trifluoromethyl, trifluoromethoxy, —OR$^{12}$, —OC(O)R$^{12}$, —C(O)R$^{12}$, —NR$^{12}$R$^{13}$, —NR$^{13}$C(O)R$^{12}$, —C(O)NR$^{12}$R$^{13}$, cyano, —C(O)OR$^{13}$, —SR$^{12}$, or —(CR$^{13}$R$^{14}$)$_t$(C$_6$–C$_{10}$ aryl), said aryl R$^{20}$ group being substituted by 1 to 4 R$^6$ groups, n is an integer selected from 1 to 3, and wherein R$^1$, R$^2$, R$^3$, R$^4$, R$^5$, R$^6$, R$^7$, R$^9$, R$^{12}$, and R$^{13}$ are as defined above;

b) applying a portion or all of the racemic mixture from step (a) to a chiral separation apparatus, under conditions suitable for separation of chiral molecules, and obtaining separated (+) and (–) enantiomers of formula 1 from said apparatus, subsequent to said conditions; and c) converting the benzylidine moiety of either the separated (+) or the separated (–) enantiomer of formula 1 from step (b) with an amine moiety R$^8$, wherein R$^8$ is as defined above, thereby obtaining a separated (+) or (–) enantiomer of a compound of formula 2.

The compounds of formula 2 possess utility in that they are inhibitors of the enzyme farnesyl protein transferase. The compounds of formula 2 encompass the compound of the invention (+)-6-[amino-(6-chloro-pyridin-3-yl)-(3-methyl-3H-imidazol-4-yl) -methyl]-4-(3-cloro-penyl)-1-cyclopropylmethyl-1H-quinolin-2-one, and hence the method described in the preceding paragraph can be used to synthesize (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one.

In one embodiment of the above-described method, the racemic mixture of step (a) is obtained by converting to (+) and (–) enantiomers of formula 1, (+) and (–) enantiomers of formula 2 in a racemic mixture

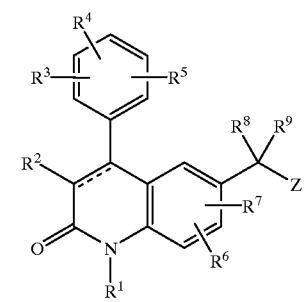

wherein Z, R$^1$, R$^2$, R$^3$, R$^4$, R$^5$, R$^6$, R$^7$, and R$^9$ are the same as those selected for Z, R$^1$, R$^2$, R$^3$, R$^4$, R$^5$, R$^6$, R$^7$, and R$^9$ in claim 9, and wherein R$^8$ is NR$^{12}$R$^{13}$, R$^{12}$ being selected from H, C$_1$–C$_{10}$ alkyl, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(C$_6$–C$_{10}$ aryl), and —(CR$^{13}$R$^{14}$)$_t$(4–10 membered heterocyclic), said cycloalkyl, aryl and heterocyclic R$^{12}$ groups being optionally fused to a C$_6$–C$_{10}$ aryl group, a C$_5$–C$_8$ saturated cyclic group, or a 4–10 membered heterocyclic group, and said R$^{12}$ substituents, except H but including any optional fused rings, optionally being substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$—NR$^{13}$R$^{14}$, hydroxy, C$_1$–C$_6$ alkyl, and C$_1$–C$_6$ alkoxy, each R$^{13}$ and R$^{14}$ being independently H or C$_1$–C$_6$ alkyl, and where R$^{13}$ and R$^{14}$ are —(CR$^{13}$R$^{14}$)$_q$ or —(CR$^{13}$R$^{14}$)$_t$ each being independently defined for each iteration of q or t in excess of 1, and each t being independently an integer from 0 to 5 and each q being independently an integer from 1 to 5.

The conversion of the (+) and (−) enantiomers of formula 2 to the (+) and (−) enantiomers of formula 1 in one embodiment comprises reacting the racemic mixture comprising the (+) and (−) enantiomers of formula 2 with a benzaldehyde of the formula 3

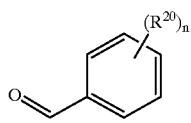

3 wherein R$^{20}$ is H, C$_1$–C$_{10}$ alkyl, C$_2$–C$_{10}$ alkenyl, C$_2$–C$_{10}$ alkynyl, halo, nitro, trifluoromethyl, trifluoromethoxy, —OR$^{12}$, —OC(O)R$^{12}$, —C(O)R$^{12}$, —NR$^{12}$R$^{13}$, —NR$^{13}$C(O)R$^{12}$, —C(O)NR$^{12}$R$^{13}$, cyano, —C(O)OR$^{13}$, —SR$^{12}$, or —(CR$^{13}$R$^{14}$)$_t$(C$_6$–C$_{10}$aryl), said aryl R$^{20}$ group being substituted by 1 to 4 R$^6$ groups; n is an integer selected from 1 to 3; each R$^{12}$ is independently selected from H, C$_1$–C$_{10}$ alkyl, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic R$^{12}$ groups optionally being fused to a C$_6$–C$_{10}$ aryl group, a C$_5$–C$_8$ saturated cyclic group, or a 4–10 membered heterocyclic group; and the foregoing R$^{12}$ substituents, except H but including any optional fused rings, optionally being substituted by 1 to 3 substituents independently selected from halo, cyano, nitro, trifluoromethyl, trifluoromethoxy, azido, —C(O)R$^{13}$, —C(O)OR$^3$, —OC(O)R$^{13}$, —NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy; each t is independently an integer from 0 to 5 and each q is independently an integer from 1 to 5; and each R$^{13}$ and R$^{14}$ is independently H or C$_1$–C$_6$ alkyl, and where R$^{13}$ and R$^{14}$ are as —(CR$^{13}$R$^{14}$)$_q$ or —(CR$^{13}$R$^{14}$)$_t$ each is independently defined for each iteration of q or t in excess of 1.

In one embodiment, for the compound of formula 3, R$^{20}$ is H or —OR$^{12}$, and R$^{12}$ is C$_1$–C$_{10}$ alkyl. For example, R$^{20}$ is methoxy or ethoxy. In another embodiment, n is 1 or 2. In another embodiment, n is 1 and R$^{20}$ is not H.

The reaction of the compound of formula 2 with the benzaldehyde molecule of formula 3 to form a racemate of formula 1 can be by condensation at ambient temperature under acidic conditions, for example in acetic acid. The removal of the benzylidine group of one of the separated enantiomers of the compound of formula 1 subsequent to chiral molecule separation of the racemate of the compound of formula 1 to form an amino group is by acidic conditions, such as by addition of hydrochloric acid.

The invention also relates to the compound (+)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, prepared by:

(a) obtaining a racemic mixture comprising (+) and (−) enantiomers of a compound of formula 1a

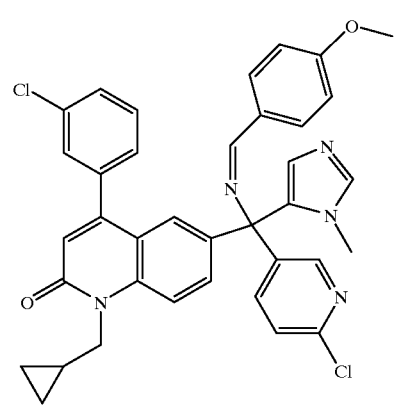

1a (b) applying a portion or all of the racemic mixture from step (a) to a chiral separation apparatus, under conditions suitable for separation of chiral molecules, and obtaining separated (+) and (−) enantiomers of formula 1a from said apparatus; and (c) converting the benzylidene moiety of the (+) enantiomer from step (b) into an amine moiety, thereby obtaining the compound (+)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one.

The invention also relates to the compound (−)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, prepared by:

(a) obtaining a racemic mixture comprising (+) and (−) enantiomers of a compound of formula 1a

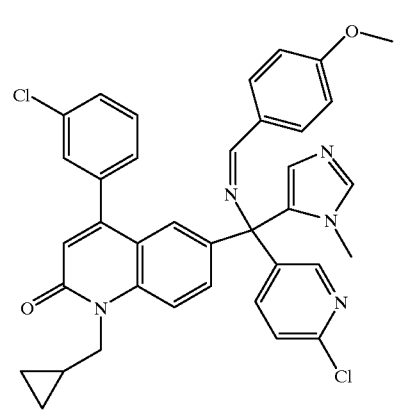

1a (b) applying a portion or all of the racemic mixture from step (a) to a chiral separation apparatus, under conditions suitable for separation of chiral molecules, and obtaining separated (+) and (−) enantiomers of formula Ia from said apparatus; and (c) converting the benzylidene moiety of the (−) enantiomer from step (b) into an amine moiety, thereby obtaining the compound (−)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "cycloalkyl", as used herein, unless otherwise indicated, includes cyclic alkyl moieties wherein alkyl is as defined above. Multicyclic, such as bicyclic and tricyclic, groups are included in this definition.

The term "alkenyl", as used herein, unless otherwise indicated, includes alkyl moieties having at least one carbon-carbon double bond wherein alkyl is as defined above.

The term "alkynyl", as used herein, unless otherwise indicated, includes alkyl moieties having at least one carbon-carbon triple bond wherein alkyl is as defined above. Examples of alkynyl groups include, but are no limited to, ethynyl and 2-propynyl.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "heterocyclic", as used herein, unless otherwise indicated, means aromatic and non-aromatic heterocyclic groups (including saturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or multicyclic, for example bicyclic (which may comprise non-aromatic and/or aromatic rings). Preferably, bicyclic heterocyclic groups of this invention contain 6–9 members in their ring systems. Monocyclic heterocyclic groups of this invention preferably contain 5 or 6 members. Aromatic multicyclic heterocyclic groups include benzo-fused ring systems. The heterocyclic groups of this invention can also include ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, piperidinyl, 1,2,3,6-tetrahydropyridinyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

DETAILED DESCRIPTION OF THE INVENTION

In the following Schemes and Examples, "Et" represents an ethyl moiety, and "Me" represents a methyl moiety. Hence, for example, "OEt" means ethoxy. Also, "THF" means tetrahydrofuran, and "DMF" means dimethylformamide. The term "rt" stands for room temperature. "HOAc" mean acetic acid. "DCM" is dichloromethane.

Compounds of formula 1 and formula 2, and enantiomers thereof, including the compound of the invention (+)-6-[amino-(6-chloro-pyridin-3-yl)-(3-methyl-3H-imidazol-4-yl) -methyl]-4-(3-chloro-phenyl)-1-cyclopropylmethyl-1H-quinolin-2-one, may be prepared according to the following Schemes 1 through 4:

Scheme 1

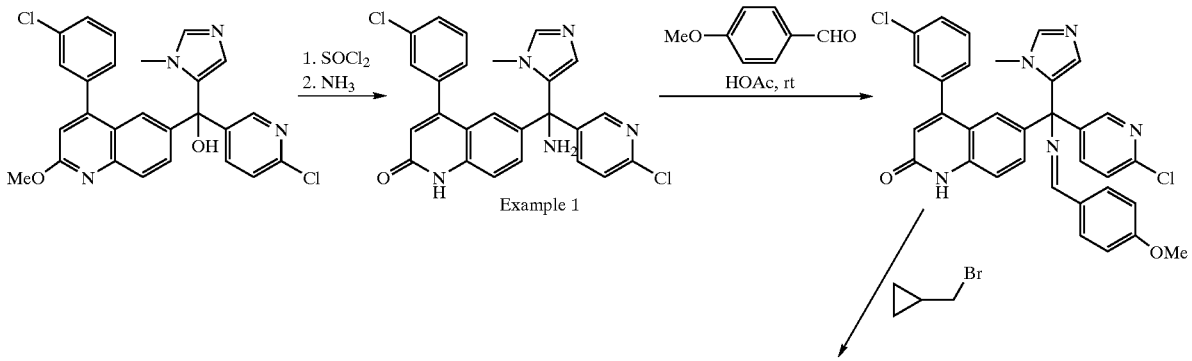

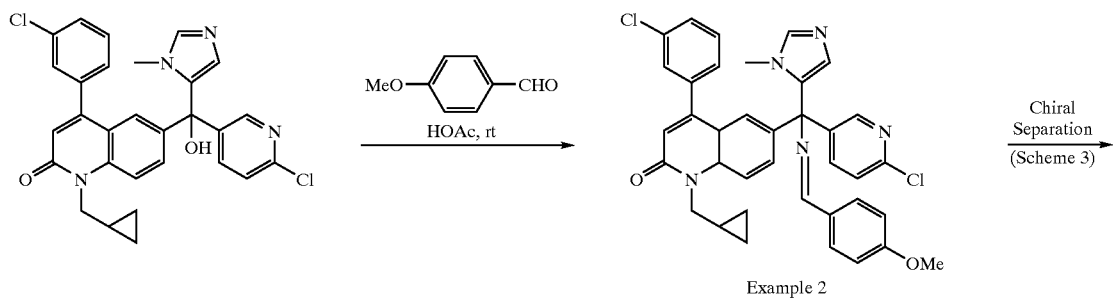
Scheme 2
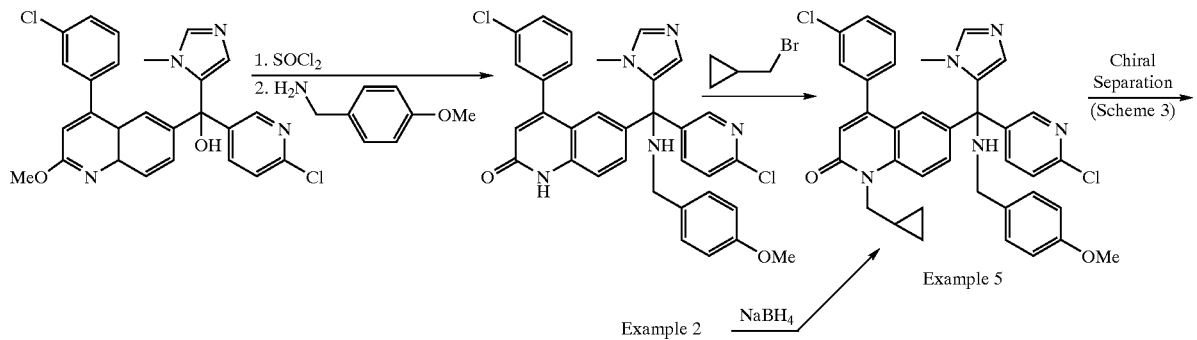
Scheme 3
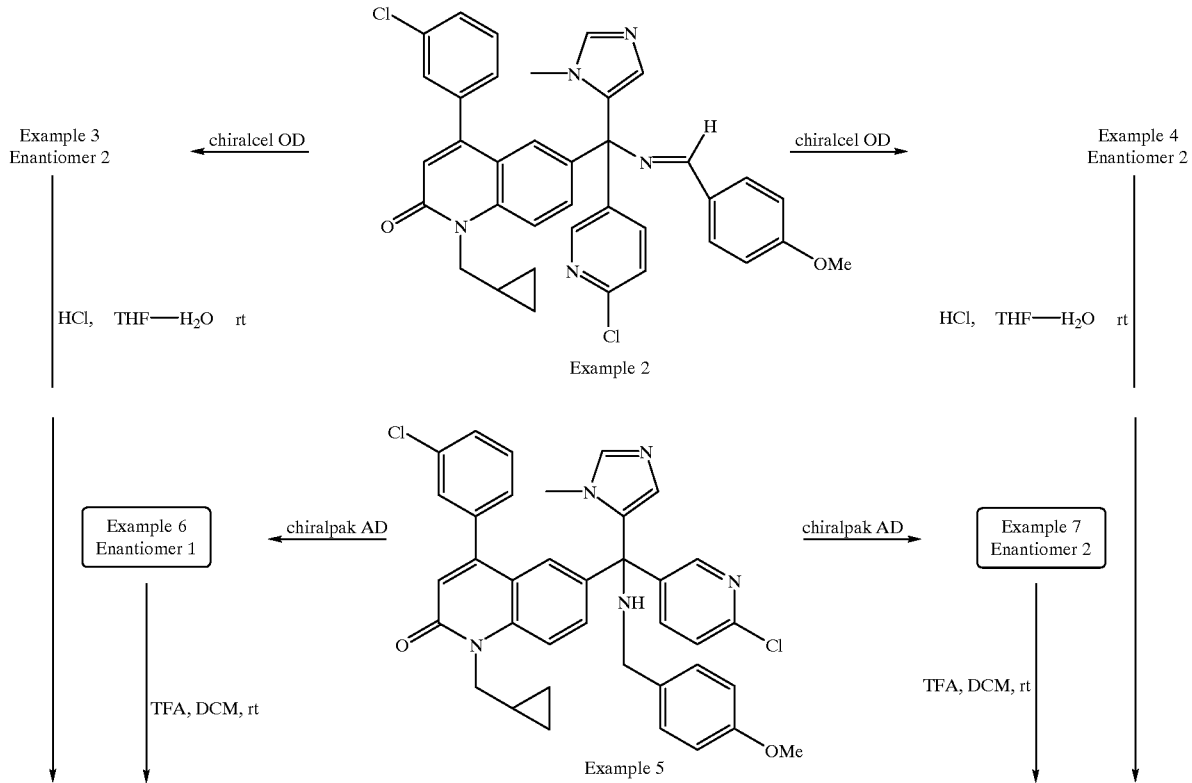

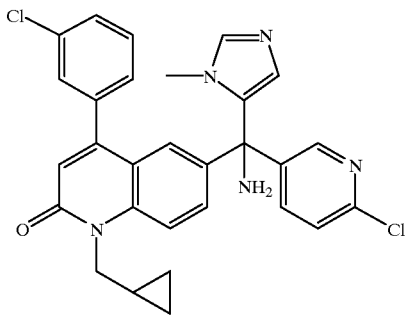

Example 9
Enantiomer 2

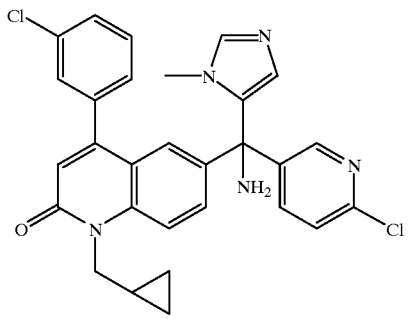

Example 8
Enantiomer 1

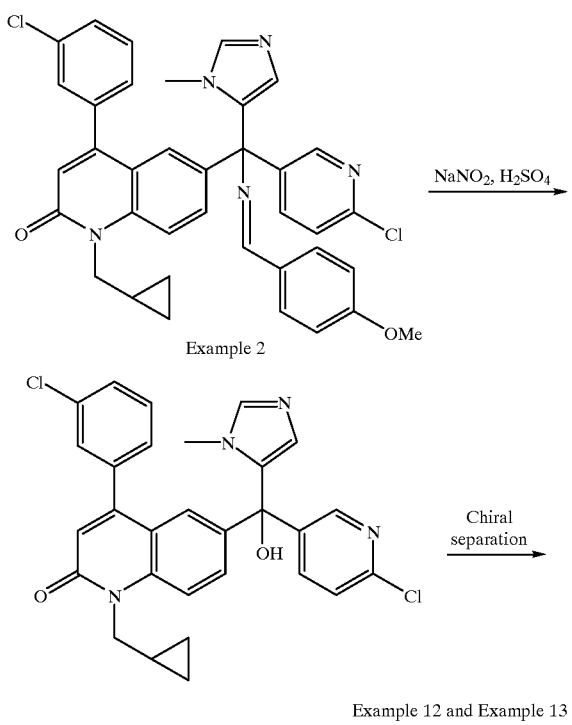

The above Schemes 1 through 4 illustrate non-limiting examples of the claimed methods of the invention.

Referring to Scheme 1, compounds of formula 2, exemplified by Example 1 in the Scheme, can be prepared from corresponding 2-alkoxy quinoline compounds by addition of thionyl chloride under an atmosphere of $N_2$.

Compounds of formula 2 can also be prepared as described in U.S. Pat. No. application Ser. No. 09/501,163, filed Feb. 9, 2000 and published as WO 00/47574, both of which are hereby incorporated in their entireties by reference.

The compound of formula 2 is condensed with a benzaldehyde compound of formula 3, such as p-anisaldehyde, to form a racemate of formula 1. The condensation can be in acidic conditions, such as in acetic acid, at ambient temperature. This racemate of formula 1 can optionally be derivatized to form other racemates of formula 1, such as the title compound of Example 2, prior to chiral molecule separation (Scheme 3).

As an alternative to chiral molecule separation of the benzylidine molecule of formula 1, a compound of formula 2 wherein $R^8$ comprises a benzylamino group can be separated on a chiral column (see Scheme 2), for subsequent formation of a compound of formula 2 wherein $R^8$ is —$NH_2$, —$NH(C_1-C_{10}$ alkyl), or —$N(C_1-C_{10}$ alkyl)($C_1-C_{10}$ alkyl) (as in Scheme 3). Referring to Scheme 2, the benzylamino compound of formula 2 can be prepared from the corresponding benzylidine compound, exemplified by Example 2 in Scheme 2, by addition of sodium borohydride to the benzylamino compound in methanol. Alternatively, the benzylamino compound of formula 2 can be prepared by treating the (6-hydroxymethyl)2-alkoxy quinoline compound with thionyl chloride under an atmosphere of dry nitrogen to form the quinolinone, followed by condensation with a benzylamino compound optionally substituted on the phenyl group, such as p-methoxybenzylamine. This condensation can occur at a temperature of about –78° C., under an atmosphere of dry nitrogen.

Referring to Scheme 3, either the benzylamino compound of formula 2, or the benzylidine of formula 1, can be applied to a chiral molecule separation column. The resulting (+) and/or (−) enantiomer of either the benzylamino compound of the benzylidine compound can be converted to an enantiomer of a compound of formula 2 wherein $R^8$ is —$NH_2$, —$NH(C_1-C_{10}$ alkyl), or —$N(C_1-C_{10}$ alkyl)($C_1-(_{10}$ alkyl). The benzylidine moiety is converted to an amino group under acidic conditions, for example by addition of hydrochloric acid. The benzylamino group is converted to an amino group also under acidic conditions, for example by addition of TFA.

Scheme 4 illustrates preparation of the dihydrochloride salt of an enantiomer of a compound of formula 2 wherein $R^8$ is —$NH_2$, —$NH(C_1-C_{10}$ alkyl), or —$N(C_1-C_{10}$ alkyl) ($C_1-C_{10}$ alkyl) directly from chiral separation of the corresponding 6-hydroxymethyl quinolinone to (+) and (−) enantiomers.

In Schemes 1 through 4, Example 8 is (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, the compound of the invention.

The compound (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, and its pharmaceutically acceptable salts and solvates, and prodrugs of the compound, can be administered orally, transdermally (e.g., through the use of a patch), parenterally or topically. Oral administration is preferred. In general, the compound, and its pharmaceutically acceptable salts and solvates, and its prodrugs, are most desirably administered in dosages ranging from about 1.0 mg up to about 500 mg per day, preferably from about 1 to about 100 mg per day in single or divided (i.e., multiple) doses. The compound, or its salt or solvate, or a prodrug thereof, will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

For the combination therapies and pharmaceutical compositions described herein, the effective amounts of the compound of the invention and of the chemotherapeutic or other agent useful for inhibiting abnormal cell growth (e.g., other antiproliferative agent, anti-angiogenic, signal transduction inhibitor or immune-system enhancer) can be determined by those of ordinary skill in the art, based on the effective amounts for the compound described herein and those known or described for the chemotherapeutic or other agent. The formulations and routes of administration for such therapies and compositions can be based on the information described herein for compositions and therapies comprising the compound of the invention as the sole active agent and on information provided for the chemotherapeutic or other agent in combination therewith.

The compound of the invention, or its salt or solvate or prodrug, may be administered alone or in combination with pharmaceutically acceptable carriers or diluents by any of the routes previously indicated, and such administration may be carried out in single or multiple doses. More particularly, the compound of this invention or its salt or solvate or prodrug can be administered in a wide variety of different dosage forms, i.e., combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the compound of the invention, or salt thereof, in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the compound, salt, or solvate topically and this may preferably be done by way of creams, jellies, gels, pastes, ointments and the like, in accordance with standard pharmaceutical practice.

The compound of the invention may also be administered to a mammal other than a human. The dosage to be administered to a mammal will depend on the animal species and the disease or disorder being treated. The compound may be administered to animals in the form of a capsule, bolus, tablet or liquid drench. The compound may also be administered to animals by injection or as an implant. Such formulations are prepared in a conventional manner in accordance with standard veterinary practice. As an alternative, the compound may be administered with the animal feedstuff, and for this purpose a concentrated feed additive or premix may be prepared for mixing with the normal animal feed.

The compounds of formula 1 and formula 2, including the compound of the invention (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one, exhibit activity as Ras famesylabon inhibitors and are useful in the treatment of cancer and the inhibition of abnormal cell growth in mammals, including humans. The activity of the compounds of formula 1 and formula 2 as Ras farnesylation inhibitors may be determined by their ability, relative to a control, to inhibit Ras farnesyl transferase in vitro. An example of one such procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams of fresh tissue in 100 ml of sucrose/ $MgCl_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C., and then collecting the resulting supernatant. This supernatant is diluted to contain a final concentration of 50 mM Tris HCl (pH 7.5), 5 mM DTT, 0.2 M KCI, 20 $\mu$M $ZnCl_2$, 1 mM PMSF and re-centrifuged at 178,000 g for 90 minutes at 4° C. The supematant, termed "crude FTase" is assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 $\mu$l containing 50 mM N-(2-hydroxy ethyl) piperazine-N-(2-ethane sulfonic acid) (HEPES), pH 7.5, 30 mM $MgCl_2$, 20 mM KCl, 25 mM $Na_2HPO_4$, 5 mM dithiothreitol (DTT), 0.01% Triton X-100, 5% dimethyl sulfoxide (DMSO), 20 mg of crude FTase, 0.12 mM [3H]-famesyl pyrophosphate ([3H]-FPP; 36000 dpm/pmole, Amersham LifeScience), and 0.2 $\mu$M of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 150 μl of streptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with FTase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-famesyl in the presence of the test compound versus its incorporation in control wells (absence of inhibitor). $IC_{50}$ values, that is, the concentration required to produce half maximal famesylation of Bt-KTKCVIS, is determined from the dose-responses obtained.

The compound (+)-6-[amino-(6-chloro-pyridin-3-yl)-(3-methyl-3H-imidazol-4-yl) -methyl]-4-(3-chloro-phenyl)-1-cyclopropylmethyl-1H-quinolin-2-one was found to have an $IC_{50}$ value for inhibiting farnesylation of the biotinylated KTKCVIS-peptide of less than 500 nM using the above-described assay.

The following Examples are provided to illustrate aspects of the subject invention. They are not intended, nor should they be construed, to limit the invention as more fully described herein and set forth in the claims.

EXAMPLE 1

6-[Amino-(6-chloro-pyridin-3-yl)-(3-methyl-3H-imidazol-4-yl)-methy[-4-(3-chloro-phenyl)-1H-quinolin-2-one To [4-(3-chloro-phenyl)-2-methoxy-quinolin-6-yl]-(6-chloro-pyridin-3-yl)-(3-methyl-3H-imidazol-4-yl)-methanol (20.95 g, 42.76 mmol) in toluene (150 ml) under an atmosphere of dry $N_2$ was added thionyl chloride (31.19 ml, 427 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 ml) and to this solution at −78° C. was bubbled ammonia gas ($NH_3$) for 10 minutes. The reaction mixture was stirred at ambient temperature under an atmosphere of $N_2$ for an additional 1.5 hours. After removal of THF, the product mixture was partitioned between $CHCl_3$ and water. The organiclayer was washed, dried over $MgSO_4$ and concentrated under vacuum to give the crude product. It was chromatographed on silica gel with $CHCl_3$ then MeOH—$CHCl_3$-$NH_4OH$ (2:98:0.1 to 7:93:0.1) as eluents to afford the title compound (17.89 g, 88% yield). C.l. m/z 473.8 [M+1].

EXAMPLE 2

4-(3-Chloro-Phenyl-6[(6-chloro-pyridin-3-yl)-[(4methoxy-benzylidene)-amino]-(3-methyl-3H-imidazol-4-yl)-methyl]-1-cyclopropylmethyl-1H-quinolin-2-one 2A. 4-(3-Chloro-phenyl)-6-[-(6-chloro-pyridin-3-yl)-[(4-methoxy-benzylidene)-amino]-(3-methyl-3H-imidazol-4-yl)-methyl]-1H-quinolin-2-one To a solution of the title compound of Example 1 (11.89 g, 25.03 mmol) in acetic acid (75 ml) was added p-anisaldehyde (6.09 ml, 50.06 mmol) dropwise. The reaction mixture was stirred at ambient temperature for 4 hours after which time it was cooled to 0° C. 10 ml of ammonia hydroxide was added followed by addition of ethyl acetate. After separation, the organic layer was washed with brine, dried over $MgSO_4$ and concentrated under vacuum to yield the crude product. It was chromatographed on silica gel with MeOH—$CHCl_3$—$NH_4OH$ (1: 99:0.1 to 5:95:0.1) as eluents to afford the title compound of Example 2A as a white solid (11.58 g, 78% yield).

Cl-MS: m/z 594.1, 596.1 [M+1].

2B. 4-(3–Chloro-phenyl)-6-[(6-chloro-pyridin-3-yl) -[(4-methoxy-benzylidene)-amino]-(3-methyl-3H-imidazol-4-yl)-methyl]-1-cyclopropylmethyl-1H-quinolin-2-one To a solution of the title compound of Example 2A (10.78 g, 18.14 mmol) in THF (2.5 ml) was added (bromomethyl) cyclopropane (2.42 ml, 24.96 mmol), benzyltriethylammonium chloride (2.59 g, 11.34 mmol), sodium iodide (0.85 g, 5.67 mmol) and a solution of 40% aqueous NaOH (30 ml). The reaction mixture was heated at 65° C. for 4 hours after which time THF was removed. The crude product mixture was partitioned between $CHCl_3$ and water. The organic layer was washed with brine, dried over $MgSO_4$ and concentrated under vacuum to give the crude product. It was chromatographed on silica gel MeOH—$CHCl_3$—$NH_4OH$ (1.5:98.5:0.1 to) as the eluents to afford the title compound as a white solid (8.49 g, 13.10 mmol, 72% yield).

Cl-MS: m/z 648.1 [M+1].

EXAMPLE 3 AND EXAMPLE 4

(+) and (−) Enantiomers of 4-(3-Chloro-phenyl)-6-[(6chloro-pyridin-3-yl)-](4-methoxy-benzylidene)-amino-]-(3-methyl-3H-imidazol-4-yl)-methyl]-1-cyclopropylmethyl-1H-quinolin-2-one The title compound of Example 2 (1.322 g) was separated into its enantiomers and purified by high-performance liquid chromatography over CHIRALCEL™ OD (manufactured by Daicel Chemical Industries, LTD, Osaka, Japan) (2.2 cm×25 cm, 10 μm; eluent: Hexane/ethanol/methanol/diethylamine 80/10/10/0.1; 25° C.). Under these conditions, 0.595 g of the faster eluting enantiomer A (Example 3): (+)-4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one, and 0.511 g of the slower moving enantiomer B (Example 4): (−)-4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one were obtained. Both enantiomers were >99% optical pure.

EXAMPLE 5

4-(3-Chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one 5A. 4-(3-(3-Chloro-phenyl)-6-[(6-chloro-pyridin-3-yl)-(4-methoxy-benzylamino)-(3-methyl-3H-imidazol-4-yl)-methyl]-1H-quinolin-2-one To [4-(3-chloro-phenyl)-2-methoxy-quinolin-6-yl]-(6-chloro-pyridin-3-yl)-(3-methy-3H -imidazol-4-yl)-methanol (1.08 g, 2.21 mmol) in toluene (8.5 ml) under an atmosphere of dry $N_2$ was added thionyl chloride (1.61 ml, 22.06 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 ml) and to this solution at −78° C. was added p-methoxybenzylamine (1.44 ml, 11.03 mmol) in THF (2 ml). The reaction mixture was stirred at −78° C. for 3 hours under an atmosphere of $N_2$ for 3 hours. After removal of THF, the product mixture was partitioned between $CHCl_3$ and water. The organic layer was washed, dried over $MgSO_4$ and concentrated under vacuum to give the crude product. It was chromatographed on silica gel with MeOH—$CHCl_3$—$NH_4OH$ (2:98:0.1) as eluents to afford the title compound of Example 5A (0.482 g, 52% yield).

C.l. m/z 596.1 [M+1].

5B. 4-(3-Chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one The same procedure was used as that described in Example 2B, except that 4-(3-chloro-phenyl)-6-[(6-chloro-pyridin-3-yl)-(4-methoxy-benzylamino)-(3-methyl-3H-imidazol-4-yl) -methyl]-1H-quinolin-2-one (0.682 g, 1.14 mmol) was used in the place of 4-(3-chloro-phenyl)-6-[(6-chloro-pyridin-3-yl)-[(4-methoxy-benzylidene)-amino]-(3-methyl-3H-imidazol-4-yl) -methyl]-1H-quinolin-2-one to give the title compound (0.315 g, 0.485 mmol, 43% yield).

C.I. m/z 650.1 [M+1].

EXAMPLE 6 and EXAMPLE 7

(+) and (−) Enantiomers of 4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one The title compound of Example 5, 4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (3.05 g) was separated into its enantiomers and purified by high-performance liquid chromatography over CHRALPAK™ AD (manufactured by Daicel Chemical Industries, LTD, Osaka, Japan) (2.2 cm×25 cm, 10 µm; eluent: Hexane/ethanol/methanol/diethylamine 80/10/10/0.1; 25° C.). Under these conditions, 1.56 g of the faster eluting enantiomer A (Example 6): (+)-4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one, and 1.07 g of the slower moving enantiomer B (Example 7): (−)-4-(3-chloro-phenyl)-6-[(6-chloro-pyridin-3-yl)-(4-methoxy-benzylamino)-(3-methyl-3H-imidazol-4-yl)methyl]-1-cyclopropylmethyl-1H-quinolin-2-one were obtained. Both enantiomers were >99% optical pure.

EXAMPLE 8

(+)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one Procedure 1. Conversion of Example 4

To a solution of the title compound of Example 4, the slower moving enantiomer of 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (1.41 g, 1.74 mmol) in THF (200 ml) was added 2N hydrochloric acid (20 ml) slowly. The reaction mixture was stirred at ambient temperature for 1.5 hour after which time it was cooled to 0° C. An aqueous solution of potassium carbonate was added followed by addition of ethyl acetate. After separation, the organic layer was washed with brine, dried over $MgSO_4$ and concentrated under vacuum to give the crude product. It was chromatographed on silica gel with MeOH—$CHCl_3$—$NH_4OH$ (1:99:0.1 to 2:98:0.1) as the eluents to afford the title compound as a white solid (0.844 g, 1.59 mmol, 90% yield). It is the faster eluting enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. m/z: 530.1, 532.1 [M+1].

Procedure 2. Conversion of Example 7

To a solution of the title compound of Example 7 (the slower moving enantiomer), (−)4-(3-chloro-phenyl)-6-[(6-chloro-pyridin-3-yl)-(4-methoxy-benzyl-amino)-(3-methyl-3H-imidazol-4-yl)-methyl]-1-cyclopropylmethyl-1H-quinolin-2-one (1.07 g, 1.64 mmol) in dichloromethane (6.5 ml) was added trifluoroacetic acid (TFA, 6.5 ml) slowly at 0° C. The reaction mixture was stirred at ambient temperature for 80 minutes after which time it was diluted with DCM (10 ml) and was poured into a chilled aqueous solution of potassium carbonate. After separation, the organic layer was washed with brine, dried over $MgSO_4$ and concentrated under vacuum to give the crude product. It was chromatographed on silica gel with MeOH—$CHCl_3$—$NH_4OH$ (1.5:98.5:0.15) as the eluents to afford the title compound as a white solid (0.588 g, 1.11 mmol, 68% yield). It is the faster eluting enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. m/z: 530.1, 532.1 [M+1].

EXAMPLE 9

(−)-6[-Amino-(6-chloro-pyridin-3-yl)-(3-methyl-3H-imidazol-4-yl)-methyl]-4-(3-chloro-phenyl)-1-cyclopronylmethyl-1H-quinolin-2-one Procedure 1. Conversion of Example 3

Following the same procedure as that described in Example 8 for the conversion of Example 4, the title compound of Example 3, the faster eluting enantiomer of 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (1.98 g, 3.05 mmol) afforded the title compound as a white solid (1.51 g, 2.85 mmol, 93% yield). It is the slower moving enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. mlz: 530.1, 532.1 [M+1].

Procedure 2. Conversion of Example 6

Following the same procedure as that described in Example 8 for the conversion of Example 7, the title compound of Example 6 (the faster eluting enantiomer, (+)-4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (0.249 g, 0.384 mmol) afforded the title compound as a white solid (0.137 g, 0.252 mmol, 66% yield). It is the slower moving enantiomer of 6-[amino-(6-chloro-pyridin-3-yl)-(3-methyl-3H-imidazol-4-yl)-methyl]-4-(3-chloro-phenyl-1-cyclopropylmethyl-1H-quinolin-2-one with >98% optical purity.

C.I. mlz: 530.1, 532.1 [M+1].

EXAMPLE 10 and EXAMPLE 11

(+) and (−) Enantiomers of 4-(3-Chloro-phenyl)-6-[(6-chloro-pyridin-3-yl) -hydroxy-(3-methyl-3H-imidazol-4-yl)-methyl]-1-cyclopropylmethyl-1H-quinolin-2-one To a solution of the title compound of Example 2 (4.31 g, 6.64 mmol) in THF (30 ml) was added 38 ml of 1N sulfuric acid. After the mixture was cooled to 0° C., a solution of sodium nitrite (NaNO$_2$, 1.45 g, 20.99 mmol) in water (10 ml) was added dropwise. The reaction mixture was stirred at ambient temperature for 7 hours after which time ethyl acetate was added. The organic layer was washed with saturated potassium carbonate, brine, dried over MgSO$_4$ and concentrated under vacuum to give the crude product. It was chromatographed on silica gel with MeOH—CHCl$_3$—NH$_4$OH (2:98:0.1) as the eluents to afford 4-(3-chloro-phenyl)-6-[(6-chloro-pyridin-3-yl)-hydroxy-(3-methyl-3H-imidazol-4-yl)-methyl]-1cyclopropylmethyl-1H-quinolin-2-one as a white solid (3.32 g, 94% yield).

Cl-MS: m/z 530.9 [M+1].

(+/−)-4-(3-Chloro-phenyl)-6-[(6-chloro-pyridin-3-yl)-hydroxy-(3-methyl-3H-imidazol-4-yl)-methyl]-1-cyclopropylmethyl-1H-quinolin-2-one (3.002 g) was separated into its enantiomers and purified by high-performance liquid chromatography over CHIRALCEL™ OD (manufactured by Daicel Chemical Industries, LTD, Osaka, Japan) (2.2 cm×25 cm, 10 μm; eluent: Hexane/ethanol/methanol 85/7.5/7.5; 25° C.). Under these conditions, 1.14 g of the faster eluting enantiomer A, (Example 10): (−)-4-(3-chloro-phenyl)-6-[(6-chloro-pyridin-3-yl) -hydroxy-(3-methyl-3H-imidazol-4-yl)-methyl]-1-cyclopropylmethyl-1H-quinolin-2-one and 0.7 g of the slower moving enantiomer B (Example 11): (+-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one were obtained.

Both enantiomers were >98% optically pure.

EXAMPLE 12

(+)-6-[Amino-(6-chloro-pyridin-3-yl)-(3-methyl-3H-imidazol-4-yl)-methyl]-4-(3-chloro-phenyl)-1-cyclopropylmethyl-1H -quinolin-2-one dihydrochloride salt To a solution of (+)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one (0.844 g, 1.59 mmol) in DCM (10 ml) was added a solution of HCl in ethyl ether (1M, 4,77 ml, 4.77 mmol). The slurry solution was stirred for 2 hours. After filtration, the title compound of Example 12 was obtained as a white solid (0.78 g, 1.29 mmol, 81.4% yield).

EXAMPLE 13

(−)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, dihydrochloride salt Following the same procedure as that described in Example 12, (−)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one (0.252 g, 0.474 mmol) generated the dihydrochloride salt as a white solid (0.167 g, 0.28 mmol, 58% yield).

EXAMPLE 14

6-[Amino-(6-methyl-pyridin-3-yl)-(3-methyl-3H-imidazol-4-yl)-methyl]-4-(3-chloro-phenyl)-1-methyl-1H-quinolin-2one 14A. 6-[Amino-(6-methyl-pyridin-3-yl)-(3-methyl-3H-imidazol-4-yl)-methyl]-4-(3-chloro-phenyl)-1 H-quinolin-2-one To [4-(3-chloro-phenyl)-2-methoxy-quinolin-6-yl]-(6-methyl-pyridin-3-yl)-(3-methyl-3H-imidazol-4-yl)-methanol (0.118 g, 0.251 mmol) in toluene (5 ml) under an atmosphere of dry N$_2$ was added thionyl chloride (0.18 ml, 2.51 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 mL) and to this solution at −78° C. was bubbled ammonia gas (NH$_3$) for 10 minutes. The reaction mixture was stirred at ambient temperature under an atmosphere of N$_2$ for additional 1.5 hours. After removal of THF, the product mixture was partitioned between CHCl$_3$ and water. The organic layer was washed, dried over MgSO$_4$ and concentrated under vacuum to give a brown solid. This was chromatographed on silica gel with CHCl$_3$ then MeOH—CHCl$_3$—NH$_4$OH (5:95:0.1 to 10:89:1) as eluents to afford the title compound of Example 14A as a white solid (53 mg, 0.116 mmol, 46.4% yield).

C.I. m/z 456.3 [M+1].

14B 6-[Amino-(6-methyl-pyridin-3-yl)-(3-methyl-3H-imidazol-4-yl)-methy]-4-(3-chloro-phenyl)-1-methyl-1H-quinolin-2-one To a solution of the title compound of Example 14A 51A (26 mg, 0.057 mmol) in THF (2.5 ml) was added a solution of 40% aqueous NaOH (0.1 ml), benzyltriethylammonium chloride (6.5 mg. 0.074 mmol) and methyl iodide (0.0046 ml, 0.0743 mmol). The reaction mixture was stirred at ambient temperature for 3 hours after which time THF was removed. The crude product mixture was partitioned between CHCl$_3$ and water. The organic layer was washed with brine, dried over MgSO$_4$ and concentrated under vacuum to give the crude product. It was purified by thin layer chromatography with MeOH—CHCl$_3$—NH$_4$OH (5:95:0.1) as the mobile phase to afford the title compound as a white solid (14.4 mg, 0.031 mmol, 54% yield).

CI-MS: mlz 470.0 [M+1].

EXAMPLE 15

6-[Amino-(6-methyl-pyridin-3-yl)-(3-methyl-3H-imidazol-4-yl)-methyl]-4-(3-chloro-phenyl)-1-cyclopropylmethyl-1H-quinolin-2-one To a solution of the title compound of Example 51A (26 mg, 0.057 mmol) in THF (2.5 ml) was added (bromomethyl) cyclopropane (0.0075 ml, 0.080 mmol), benzyltriethylammonium chloride (6.5 mg. 0.0286 mmol), sodium iodide (2.57 mg, 0.0171 mmol) and a solution of 40% aqueous NaOH (0.57 ml). The reaction mixture was heated at 65° C. for 3 hours after which time THF was removed. The crude product mixture was partitioned between CHCl$_3$ and water.

The organic layer was washed with brine, dried over MgSO₄ and concentrated under vacuum to give the crude product. It was chromatographed on silica gel with MeOH—CHCl₃—NH₄OH (2:98:0.1 to 5:95:0.1) as the eluents to afford the title compound as a white solid (11 mg, 0.022 mmol, 38% yield).

Cl-MS: mlz 510.3 [M+1].

EXAMPLE 16

6-[Amino-(pyridin -3-yl)-(3-methyl-3H-imidazol-4-yl)-methyl]-4-(3-chlorophenyl)-1-cyclopropylmethyl-1H-qiuinolin-2-one To a solution of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one (0.408 g, 0.77 mmol) in pyridine (0.77 ml) was added trichloroethyl chloroformate (0.159 ml, 1.15 mmol) at 0° C. The reaction mixture was gradually warmed to room temperature and stirred overnight. After removal of pyridine, the product mixture was taken into dichloromethane and water. After separation, the organic layer was washed with brine, dried over MgSO₄ and concentrated under vacuum to give the crude product. It was chromatographed on silica gel with MeOH—CHCl₃—NH₄OH (1:99:0.1) as the eluents to afford the trichloroethyl carbamate as a white solid (0.451 g, 0.64 mmol, 83% yield).

CI-MS: m/z 705.8, 708.0 [M+1].

To a solution of the trichloroethyl carbamate (34 mg, 0.048 mmol) in formic acid (0.96 ml) was added zinc powder (87 mg). The reaction mixture was stirred at ambient temperature for 15 minutes. After addition of methanol, the mixture was filtered through the celite, followed by a saturated solution of potassium carbonate. The filtrated was evaporated and was extracted with chloroform. The organic layer was washed with brine, dried over MgSO₄ and concentrated under vacuum to give the crude product. It was chromatographed on silica gel with MeOH—CHCl₃—NH₄OH (2:98:0.) as the eluents to afford the title compound as a white solid (25 mg, 100% yield).

CI-MS: m/z 496.1 [m+1].

What is claimed is:

1. The compound (+)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, or a pharmaceutically acceptable salt, solvate, prodrug, or isotopically-labelled derivative thereof.

2. The compound (+)-6-[-Amino-(6-chloro-pyridin-3-yl)-(3-methyl-3H-imidazol-4-yl)-methyl]-4-(3-chloro-phenyl)-1-cyclopropylmethyl-1H-quinolin-2-one.

3. A method of inhibiting abnormal cell growth in a mammal comprising administering to said mammal an amount of a compound of claim 1 that is effective in inhibiting abnormal cell growth.

4. A method of inhibiting abnormal cell growth in a mammal which comprises administering to said mammal an amount of a compound of claim 1, in combination with an amount of a chemotherapeutic, wherein the amount of the compound of claim 1 and the amount of the chemotherapeutic are together effective to inhibit abnormal cell growth.

5. A pharmaceutical composition for inhibiting abnormal cell growth in a mammal comprising an amount of a compound of claim 1 that is effective in inhibiting abnormal cell growth, and a pharmaceutically acceptable carrier.

6. A pharmaceutical composition for inhibiting abnormal cell growth in a mammal which comprises an amount of a compound of claim 1, in combination with an amount of a chemotherapeutic, wherein the amount of the compound of claim 1 and the amount of the chemotherapeutic are together effective to inhibit abnormal cell growth.

7. A pharmaceutical composition for treating a disease or condition selected from lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors, Hodgkin's Disease, cancer of the esophagus, cancer of the small intestine, cancer of the endocrine system, sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter, pediatric malignancy, neoplasms of the central nervous system, Barrett's esophagus (pre-malignant syndrome), neoplastic cutaneous disease, psoriasis, mycoses fungoides, benign prostatic hypertrophy, human papilloma virus (HPV), and restenosis in a mammal comprising an amount of a compound of claim 1 that is effective in treating said disease, and a pharmaceutically acceptable carrier.

8. A pharmaceutical composition for treating abnormal cell growth in a mammal comprising (a) an amount of a compound of claim 1, (b) an amount of at least a substance selected from the group consisting of MMP-2 inhibitors, MMP-9 inhibitors, signal transduction inhibitors, antiproliferative agents, and agents capable of blocking CTLA4, and (c) a pharmaceutically acceptable carrier, wherein the amounts of (a) and (b) are together effective in treating abnormal cell growth.

* * * * *